(12) United States Patent
Wouters (10) Patent No.: US 10,191,002 B2
(45) Date of Patent: Jan. 29, 2019

(54) GAS SENSOR WITH FREQUENCY MEASUREMENT OF IMPEDANCE

(71) Applicant: Stichting IMEC Nederland, Eindhoven (NL)

(72) Inventor: Daan Wouters, Geldrop (NL)

(73) Assignee: Stichting IMEC Nederland, Eindhoven (NL)

(*) Notice: Subject to any disclaimer, the term of this patent is extended or adjusted under 35 U.S.C. 154(b) by 59 days.

(21) Appl. No.: 15/202,685

(22) Filed: Jul. 6, 2016

(65) Prior Publication Data

US 2017/0010231 A1    Jan. 12, 2017

(30) Foreign Application Priority Data

Jul. 6, 2015 (EP) .................................. 15175558

(51) Int. Cl.
*G01N 27/06* (2006.01)
*G01N 27/02* (2006.01)
(Continued)

(52) U.S. Cl.
CPC ............. *G01N 27/06* (2013.01); *G01N 27/02* (2013.01); *G01N 27/22* (2013.01);
(Continued)

(58) Field of Classification Search
CPC .. G01N 27/06; G01N 33/0047; G01N 33/004; G01N 27/026; G01N 27/4045; G01N 27/22; G01N 27/02
(Continued)

(56) References Cited

U.S. PATENT DOCUMENTS

2010/0133120 A1   6/2010   Varney et al.
2013/0153442 A1*   6/2013   Chen .................. G01N 27/4045
                                                            205/786.5
(Continued)

FOREIGN PATENT DOCUMENTS

EP      2743691      6/2014
WO    2013/060773   5/2013
WO    2013/127985   9/2013

OTHER PUBLICATIONS

European Search Report dated Jan. 4, 2016 for European Application No. 15175558.4.
(Continued)

*Primary Examiner* — Melissa J Koval
*Assistant Examiner* — Trung Nguyen
(74) *Attorney, Agent, or Firm* — McDonnell Boehnen Hulbert & Berghoff LLP (57) ABSTRACT

The present disclosure relates to methods and devices for gas sensing. A gas sensor includes a sensing element comprising at least an ionic liquid. The gas sensor also includes a set of electrodes for polarizing the sensing element and an electric power source for powering the set of electrodes, thus generating an impedimetric response signal from the sensing element. The gas sensor additionally includes readout circuitry for separately analyzing resistive and capacitive components in the impedimetric response signal. A method includes exposing a gas sensor to a gas. The gas sensor includes a sensing element including at least an ionic liquid. The method also includes polarizing the sensing element with an electrical signal at a first frequency, measuring an impedimetric response signal of the sensing element, separating the signal into resistive and capacitive components, and determining the composition of the gas based at least on the resistive and capacitive components.

18 Claims, 4 Drawing Sheets

(51) Int. Cl.
  *G01N 27/404* (2006.01)
  *G01N 27/22* (2006.01)
  *G01N 33/00* (2006.01)
(52) U.S. Cl.
  CPC ....... *G01N 27/4045* (2013.01); *G01N 27/026* (2013.01); *G01N 33/004* (2013.01); *G01N 33/0047* (2013.01)
(58) Field of Classification Search
  USPC ...... 324/500, 514, 756.01–758.01, 600, 681, 324/76.11, 87, 459, 464, 122; 205/780.5, 205/792, 779; 600/345–350, 365–366
  See application file for complete search history.

(56) References Cited

U.S. PATENT DOCUMENTS

| | | |
|---|---|---|
| 2014/0002111 A1 | 1/2014 | Potyrailo et al. |
| 2014/0025313 A1 | 1/2014 | Potyrailo et al. |
| 2015/0014167 A1* | 1/2015 | Dziallas ............. G01N 27/4074 204/415 |

OTHER PUBLICATIONS

Ishizu et al., "Carbon Dioxide Gas Sensor With Ionic Gel," Transducers 2013, Barcelona, Spain, Jun. 16-20, 2013, pp. 1633-1636.
Wang et al., "Methane Recognition and Quantification by Differential Capacitance at the Hydrophobic Ionic Liquid-Electrified Metal Electrode Interface," Journal of the Electrochemical Society, 160 (6) B83-B89 (2013).

* cited by examiner

GAS SENSOR WITH FREQUENCY MEASUREMENT OF IMPEDANCE

CROSS-REFERENCE TO RELATED APPLICATIONS

The present application is a non-provisional patent application claiming priority to European Patent Application No. EP 15175558.4, filed on Jul. 6, 2015, the contents of which are hereby incorporated by reference.

FIELD OF THE DISCLOSURE

The present disclosure relates to the field of gas and vapor sensing. More specifically it relates to devices and methods to measure concentration of gases, such as vapors, in ambient.

BACKGROUND

Vapor sensors and smoke detectors, humidity sensors or in general gas sensors are widely used, and the extent of their applicability ranges from industrial or hospital environments and building automation systems to automobile applications or consumer products. Some of these gas sensing systems are based on absorption or sorption of a target gas on a sensing element, which causes a change in the sensing element's properties. These properties are monitored and the changes can be visualized, recorded, or integrated in an automation system. For example, if a sensor detects high concentrations of a determined gas, e.g. $CO_2$, an alarm may be set off.

Some types of sensors utilize the electric properties of a sensing material, which probes the environmental gas by acting as a sorption layer. For example, the sensing material may be an ionic liquid (IL). Ionic liquids are liquids containing or being formed mainly by ions, for example salts in liquid state. ILs are electrically conductive. The resistance of ILs depends on factors such as composition or, notably, viscosity. Upon sorption and dissolution of gas particles in the ionic liquid, the electrical properties of the IL change, hence changing the resistance. In some cases, direct use of ionic liquids as sorption layer may be disadvantageous or even impossible because of flow of the liquid on the sensor surface, and the disability to create thin enough layers, worsening response time. In some cases, the contact area between sorption layer and electrodes may not be constant, and signal may be erroneous or lost. In some cases, conventional systems incorporate the ionic liquid in a gel and producing a thin gel layer as sensing layer in the sensor device. The properties of the IL in the gel, e.g. good analyte solubility and good response in impedance to sorbed species, remain favorable for gas and vapor sensing. Nonetheless, the problem with selectivity and sensitivity remains. Most of the IL-based sensors have low selectivity, because many gasses interact with ionic liquids. This leads to crossed signals, which may result in false reading produced by a mixture of two different gasses. For example, the conductivity of ionic liquids drops with both $CO_2$ and humidity, hence in a wet environment the measurement of $CO_2$ will contain a lot of noise from the environmental water. Moreover, the sensitivity is good only for a limited range in most IL sensors. For instance, humidity sensors may be optimized for either environments with high humidity or with low humidity, and they often fail if the environmental conditions diverge from their optimal range of measurement. It is usually necessary to provide a plurality of sensors, each optimized for a different range, but this is costly and does not solve the problem of cross-sensitivity.

SUMMARY

It is an object of embodiments of the present disclosure to provide a gas sensor with good sensitivity and selectivity, for example with improved sensitivity and selectivity compared to conventional gas sensors.

In a first aspect, embodiments of the present disclosure relate to a gas sensor comprising at least one sensing element comprising at least an ionic liquid, polarizable by at least one set of electrodes, the electrodes being connectable to an electric power source. The power source is adapted for powering the at least one set of electrodes, e.g. by generating a signal in the electrodes, thus generating an impedimetric response signal from the sensing element. The gas sensor further comprises readout circuitry for separately analyzing resistive and capacitive components in the impedimetric response signal. Good stability of the sensing element may be attained by electrode or substrate patterning.

Example embodiments of the present disclosure provide a gas sensor with good response and analyte solubility. In some cases, measurements involving multiple gases may be obtained simultaneously with good selection, e.g. several gasses can be simultaneously detected in a single measurement using a single sensor, reducing cross-sensitivity. Furthermore, examples described herein may provide good selectivity as well as good sensitivity. Yet further, some embodiments provide a stable sensing element.

In some embodiments of the present disclosure, the sensing element comprises an ionic liquid gel, comprising ionic liquid and a gellant. According to some embodiments of the present disclosure, the gellant may be selected from the group of organic gels, inorganic gels such as polymers, or a mixture thereof. These embodiments may present a stable sensing element by preventing the ionic liquid from flowing into non-sensitive zones of the sensor, further also allowing measurements be more stable, due to the possibility of deposition of thin gel layers. Good gellification and miscibility may be obtained for a wide range of different ionic liquids.

Embodiments of the present disclosure may comprise an interdigitated array of electrodes, for example an interdigitated array of microelectrodes (IDAM). As such, some embodiments may provide geometric optimization of the electrodes for measurement of the capacitive or of the resistive components of the impedance of the sensing element. In embodiments comprising IDAM, sensitivity of the sensor may be increased and the sensor may be suitable for circuit integration.

Some embodiments of the present disclosure may comprise a plurality of sensing elements, or a plurality of ionic liquids, thereby obtaining fine sensitivity tuning for a plurality of gasses. For example, different sensing elements may be adapted to have an optimized sensitivity to different ranges of gas concentrations, while still each sensor has a high sensitivity and a good, e.g. improved, selectivity. The ionic liquids may be selected from the group consisting of 1-Butyl-3-methylimidazolium bis(trifluoromethylsulfonyl) imide, 1-Hexyl-3-methylimidazolium tris(pentafluoroethyl) trifluorophosphate, and 1-butyl-1-methylpyrrolidinium tris (pentafluoroethyl) trifluorophosphate, or a mixture thereof. These particular ionic liquids present different change rate of resistance and/or capacitance for different gasses, and at different signal frequencies. The choice of ionic liquids may be optimized for a determined range of measurement or for determined conditions of measurement such as temperature and humidity. Embodiments comprising gellants may be optimized according to each particular case, as well as the ratio between IL and gellant. For example, particular embodiments of a sensor according to embodiments of the present disclosure may comprise 1-Butyl-3-methylimidazolium bis(trifluoromethylsulfonyl)imide and poly(vinylidene-co-hexafluoropropylene) in a 7:3 weight ratio, which may provide sufficient fixation for preventing the IL from spreading to non-active areas of the sensor, at an amount allowing easy handling of the sensing element, e.g. allowing easy separation of the IL gel from a substrate and placement over the electrodes. The higher the ratio, the more sticky the IL gel gets, and the more difficult it gets to separate the gel from a substrate and place it over the electrodes.

Some embodiments of the present disclosure may comprise an electric power source for providing electric AC signal with a frequency of at least 0.01 Hz, for example 0.1 Hz or even more, for example 1 MHz. The frequency of the signal may be variable. These embodiments may directly provide good selectivity between different analytes, by comparison of their impedance response with the frequency.

Some embodiments of the present disclosure may comprise at least a first and a second sensing element, wherein the first sensing element comprises a first set of electrodes comprising an interdigitated electrode array with a predetermined first geometry, and wherein the second sensing element comprises a second set of electrodes comprising an interdigitated electrode array with a predetermined second geometry different from the first geometry. In such a scenario, improved gas selectivity may be obtained with respect to existing technologies, and several sensors may be combined.

Some embodiments of the present disclosure comprising a plurality of sensing elements may further comprise an IDAM for each sensing element. These embodiments may provide a possible optimization of number and dimensions of electrodes in the array, for instance to improve and/or optimize the measurement of either the resistive component or the capacitive component of the impedance. Optimization may be performed for dedicated sensors and for more than one type of gas, based on the capacitive or resistive component of the measurement.

Some embodiments of the present disclosure may comprise a plurality of sensing elements (e.g. comprising different electrode geometries but comprising the same ionic liquid gel), and the electric power source can be further shared by the plurality of sensing elements. As such, a single electrical signal may be used, thereby reducing measurement errors.

In a second aspect of the present disclosure, a method of gas sensing is provided comprising exposing a sensor according to embodiments of the first aspect of the present disclosure to a gas or gas mixture. In a second step, the method comprises polarizing the at least one sensing element with an electric signal at a predetermined first frequency, and measuring the impedance response of the sensing element. Finally, the response is separated into the resistive and capacitive components. The analysis of the response and its components are used to derive the composition of the gas or gas mixture. The sensitivity and selectivity can be increased with respect to conventional methods, because the response of the resistive component of the sensing element impedance differs from one type of gas to another, as well as from the response of the capacitive component. In other words, analyzing the resistive component independently from the capacitive component reduces cross-sensitivity. Multiple gas detection is made possible by the use of frequency and analyzing the frequency response of the capacitive component and the resistive component, which are different for different gasses and gas mixtures.

In some embodiments, the measurement of the impedance may be repeated for at least a further frequency different from the first frequency. This would allow obtaining the impedance response, improving the response for the capacitive component, with a single sensor. For example, the frequency may be continuously varied while recording the impedance response, and the resulting response with frequency can be used to determine gas composition. The analysis of the response may be performed by comparison with known values. Methods according to the present disclosure may comprise a calibration step using a known reference.

Particular and preferred aspects of the present disclosure are set out in the accompanying independent and dependent claims. Features from the dependent claims may be combined with features of the independent claims and with features of other dependent claims as appropriate and not merely as explicitly set out in the claims.

These and other aspects of the present disclosure will be apparent from and elucidated with reference to the embodiment(s) described hereinafter.

The drawings are only schematic and are non-limiting. In the drawings, the size of some of the elements may be exaggerated and not drawn on scale for illustrative purposes.

Any reference signs in the claims shall not be construed as limiting the scope.

In the different drawings, the same reference signs refer to the same or analogous elements.

DETAILED DESCRIPTION

The present disclosure will be described with respect to particular embodiments and with reference to certain drawings but the disclosure is not limited thereto but only by the claims. The drawings described are only schematic and are non-limiting. In the drawings, the size of some of the elements may be exaggerated and not drawn on scale for illustrative purposes. The dimensions and the relative dimensions do not correspond to actual reductions to practice of the present disclosure.

The terms first, second and the like in the description and in the claims, are used for distinguishing between similar elements and not necessarily for describing a sequence, either temporally, spatially, in ranking or in any other manner. Moreover, the terms top, under and the like in the description and the claims are used for descriptive purposes and not necessarily for describing relative positions. It is to be understood that the terms so used are interchangeable under appropriate circumstances and that the embodiments described herein are capable of operation in other orientations than described or illustrated herein.

It is to be noticed that the term "comprising", used in the claims, should not be interpreted as being restricted to the means listed thereafter; it does not exclude other elements or steps. It is thus to be interpreted as specifying the presence of the stated features, integers, steps or components as referred to, but does not preclude the presence or addition of one or more other features, integers, steps or components, or groups thereof. Thus, the scope of the expression "a device comprising means A and B" should not be limited to devices consisting only of components A and B. It means that with respect to the present disclosure, the only relevant components of the device are A and B.

Reference throughout this specification to "one embodiment" or "an embodiment" means that a particular feature, structure or characteristic described in connection with the embodiment is included in at least one embodiment of the present disclosure. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to one of ordinary skill in the art from this disclosure, in one or more embodiments.

Similarly it should be appreciated that in the description of exemplary embodiments of the present disclosure, various features are sometimes grouped together in a single embodiment, figure, or description thereof for the purpose of streamlining the disclosure and aiding in the understanding of one or more aspects. This method of disclosure, however, is not to be interpreted as reflecting an intention that a given embodiment requires more features than are expressly recited in each claim. Rather, as the following claims reflect, various aspects lie in less than all features of a single foregoing disclosed embodiment. Thus, the claims following the detailed description are hereby expressly incorporated into this detailed description, with each claim standing on its own as a separate embodiment of the present disclosure.

Furthermore, while some embodiments described herein include some but not other features included in other embodiments, combinations of features of different embodiments are meant to be within the scope of the present disclosure, and form different embodiments, as would be understood by those in the art. For example, in the following claims, any of the claimed embodiments can be used in any combination.

In the description provided herein, numerous specific details are set forth. However, it is understood that some embodiments may be practiced without these specific details. In other instances, well-known methods, structures and techniques have not been shown in detail in order not to obscure an understanding of this description.

Where in embodiments of the present disclosure reference is made to a "gas", reference is made to any substance in gaseous state. Hence, vapors, smoke and fumes are understood to be included within the term "gas" in the present description.

Where in embodiments of the present disclosure reference is made to a "gellant", reference is made to any compound which congeals, clots, curdles or jellifies a liquid or, in general, confers gel properties to a liquid. In an example embodiment, the gellant may have gel properties at room temperature (e.g. under 30° C.) or higher. For example, a suitable gellant may confer gel properties to a determined ionic liquid (IL), resulting in an "IL gel". Where in embodiments of the present disclosure reference is made to a "sensing element", reference is made to the active part of a gas sensor whose properties change in response to the presence of the gas; in embodiments of the present disclosure such sensing element comprises a small amount, typically one or more layers, of IL gel comprising a mixture of a gellant or gellants and one or more ILs.

The present disclosure relates to methods and devices for gas sensing using ILs. When the IL is in contact with a gas, part of the gas dissolves in the IL, thus changing the viscosity of the IL. It has been found surprisingly that gas dissolved in the IL, in turn, causes a change not only in the resistive component R, but also in the capacitive component C, overall affecting the impedance (Z) of the IL. Impedance can be measured by an electric signal passing through the IL. In embodiments of the present disclosure, the electric signal is a variable electric signal, having a frequency of, for example, 0.1 Hz or higher. Additionally, some embodiments of the present disclosure may allow the measurement of capacitance and resistance independently, for example the simultaneous measurement of R and C variations at the same frequency of the signal.

Other variables, such as the thickness of the sensing element, may affect the resistance of the IL and delay the sensor response.

In some embodiments described herein, use of an IL gel may avoid unstable or vanishing signal in the sensor. By using an IL gel, the thickness of the IL layer is kept constant, because the gel prevents the flow of liquid away from the sensor. It further allows the deposition of sufficiently thin, stable films, while retaining the gas sorption, analyte solubility and response properties of the IL. In order to produce thin layers of IL gel, the IL may be gellified by methods known in the art, e.g. by dissolution of a suitable gellant and IL in a suitable solvent and then evaporation of the solvent. Any other suitable method may be applied to each particular gellant-IL pair.

The IL gel can be deposited on the electrodes of the sensor, thereby forming the sensing element. Deposition may be done by coating or by any other suitable technique such as printing. For example, polymer-ionic liquid gels may be deposited from a diluted solution in a common solvent by drop-casting, spin coating or inkjet printing. This may be combined with e.g. slow evaporation of the solvent, or other suitable methods.

The present disclosure is not limited to sensing elements comprising gellants. Alternatively, a thin film of IL can be obtained by using a patterned substrate or electrodes with liquid fixing properties, which fixes the IL in place, for instance by capillary forces. Gellant may be added, in a particular embodiment, in order to assist the capillary forces or, if no patterned substrate is present or no capillary forces are envisaged, as an alternative way of fixing the IL in place.

Many ionic liquids or even mixtures of ionic liquids may present different affinity and/or solubility towards different gasses. In some embodiments, non-water miscible ILs may be used. Such so-called hydrophobic ILs only dissolve a limited amount of water and when in use in a sensor, the ambient humidity in air and water content in the IL will be in equilibrium. This in contrast to fully water-miscible ionic liquids which would keep absorbing water.

In embodiments of the present disclosure, an electric signal is passed through the sensing element comprising at least an ionic liquid, for measuring its impedance. Embodiments of the present disclosure comprise measuring the sensor response of the electric signal, taking into account the combination of a resistive component (R) and a capacitive component (C). The response of the sensing element towards dissolved gasses is different for the resistive and capacitive components. An explanation is that the capacitive component of the response is an effect of the electrode/sensing element interface, whereas the resistive response may originate from a change in bulk properties of the sensing element due to the introduction of the gas particles. For these reasons, the response time of the capacitive component is larger, since dissolved gasses have to diffuse from the gas/sensing element interface to the sensing element/electrode interface.

Embodiments of the present disclosure may further comprise a system of sensors, such as a set of sensors and a readout system, each comprising a sensing element including different ionic liquids, different IL gels, or both. The plurality of sensors may comprise tailored interdigitated electrode arrays, for optimization of the measurement of the C, or of R of the impedance Z.

According to experimental observations, the impedance response is frequency-dependent, and the contributions of the resistive component R and the capacitive component C to the change in impedance (Z) vary for particular sensing element/gas pairs. Since the capacitive and resistive components of the impedimetric response vary with the gas selectivity for a given IL, the response can be obtained for more gasses by determining these individual components. For example, the components can be obtained by measuring the impedance on a single gas sensor device at different frequencies, and/or on arrays of gas sensor devices using different electrode designs optimized for measuring the capacitive or resistive component. By measuring both the resistive and capacitive component of the sensor response, a fast and highly sensitive response may be obtained. For example, the sensor may give a quick reading on the concentration range in which a particular analyte is present, and a more accurate value after a longer measurement time.

Moreover, the different responses (resistive and capacitive components) at various frequencies may be used to obtain selectivity within a single device as opposed to obtaining selectivity by operating an array of sensors with different compositions of sensing elements. One of the possible ways to obtain selectivity in a single device is to measure the response of a single sensor in time at various frequencies. Diffusion speed of analytes depend on their solubility in the IL gel, and on their particle size and geometry. Hence, the response in the bulk of the gel (resistive component) and the response at the electrode interface (capacitive component) may be different for each analyte. Due to the importance of sensitivity for the measurements at various frequencies, sensitivity may be increased or adjusted by increasing the area of contact between the electrode and the gel, for example with the use of an interdigitated array of electrodes. For example, if a sensor needs to be compact (e.g. an integrated sensor, or in microsensing applications), microelectrodes may be used, and their sensitivity may be increased by using an interdigitated array of microelectrodes (IDAM). In some embodiments of the present disclosure, micropillars may be comprised in the electrodes to keep the IL in contact with as much area of the electrode as possible.

In a first aspect, the present disclosure relates to a sensor and a sensor system for gas detection.

In embodiments of the present disclosure, the sensing element of the sensor is in contact with at least two electrodes, and the sensing element may comprise an IL gel, formed by an IL and a gellant. In particular embodiments of the present disclosure, the sensor may comprise a pair of separated microfabricated electrodes on a substrate, for instance a dielectric substrate such as a silicon oxide substrate, onto which a thin film of IL gel, forming the sensing element, is deposited. Some embodiments of the present disclosure comprise a substrate adapted to keep the IL fixed onto its surface (e.g. by capillary forces, in case of patterned substrates), in which case the gellant may not be added to the sensing element. Other substrates may be used, taking into account their properties (e.g. water absorption, resistance to corrosion, etc.) in combination with each particular application. In embodiments comprising IL gel, the IL gel may be produced by any suitable technique, and it is deposited on top of the electrodes, creating an electric contact between them. The deposition may be done by drop-casting, spin coating, by printing, or any other suitable technique.

The electrodes may further comprise an interdigitated array of electrodes, which may be formed by any suitable technique, such as patterning, laser trimming, etc. The interdigitated array may be optimized for measurement of resistive and/or capacitive components of a measurement signal. The number of electrodes, the electrode separation and other geometric characteristics can be optimized for the resistive and/or capacitive components of the sensor response. In some embodiments of the present disclosure, the interdigitated array comprises microelectrodes (IDAM).

Alternatively or additionally, a set of sensors with different electrode designs may be employed. In such sensor system, the electrodes, for instance the interdigitated array of electrodes, of at least one sensor may be tailored towards optimizing the response for the resistive component R, while for at least one other sensor, the array may be tailored towards optimizing the capacitive component C. For example, measurement of the capacitive component C may be optimized by increasing the contact area of the electrodes, e.g. interdigitated electrodes, with the sensing element (thereby making the sensor wider, for example). For example, measurement of the resistive component R may be optimized by separating the fingers of an interdigitated array of electrodes.

Alternatively or additionally, according to some embodiments of the sensor system of the present disclosure, at least some, and possibly each, of its sensing elements may be different, comprising different ILs and/or gellants. For example, some sensing elements may have a high concentration of IL and others a low concentration of the same IL, thus optimizing the system for a wider range of environmental gas concentration. Different sensing elements may comprise different ILs for increasing selectivity by reducing cross-sensitivity. For example, some may be optimized for sensing humidity while others may be used for sensing other gases like for instance methane or $CO_2$.

The electrodes are connectable to a source of electric power, such an AC/DC power source. For example, the source may provide variable frequency in a range between 1 mHz to 1 MHz, more particularly between 0.1 Hz to 1 MHz, and for example using AC bias between 0-500 mV, for example between 50 to 100 mV, and a DC bias between 0 and 1 V. As the sensing element is in contact with the electrodes, the electrodes polarize the sensing element which creates an impedimetric response signal which can be measured.

In embodiments comprising a set of sensors, these sensors may be connected to a same power source, hereby being polarizable by a same frequency, thus reducing errors of measurement. Alternatively, the set of sensors may be connected to a plurality of power sources, different sensors being connected to a different power source, thereby improving the selectivity and the speed of analysis.

In accordance with embodiments of the present disclosure, a readout system connected to the electrodes of the sensor or the electrodes of the set of sensors may be used to measure the impedimetric response signal. The readout system, which may comprise an impedance analyzer, may be integrated in a small dedicated device, it may be part of an integrated circuit, a sensor-on-chip, etc. The readout system connected to the sensor or sensor system may be used to separately measure the capacitive and resistive components. For example, C, R or both may be measured for a range of frequencies, or the variation of the impedance (e.g. the change of C, or R, or both) with time may be obtained for a frequency or a range of frequencies. The readout system may comprise analog-to-digital converters, memory modules and look-up tables, displays, etc.

In a second aspect, the present disclosure provides a method for measuring the concentration of gasses, such as vapors, in a given environment, by observing the changes in the impedance of an IL. Because the changes may depend on the diffusion rate of the analyte (e.g. the gas), the sensing element should be as static as possible, avoiding flow or thickness changes, hence an IL in gel form may be used as sensing element according to embodiments of the present disclosure. The sensing element is polarized by electrodes in contact with it, and the impedance Z of the sensing element is measured. The method may comprise independently measuring the capacitive and resistive components, and the change of R and C may be recorded for different frequencies and for different times. The method allows determining the concentration of particular gas components. By comparing the frequency response for different analytes, selectivity is improved. Various embodiments of the present disclosure may include electrodes comprising interdigitated arrays of electrodes, thereby increasing the contact area with the sensing element and allowing flexibility in the separation of the R and/or C components.

In some embodiments of the present disclosure, the impedance is measured for a range of frequencies. It is found that the impedance of the gel scales with concentration of gas in the sensing element for a number of materials, such as ethanol, water or $CO_2$, and others gasses that show good solubility into the IL. Information regarding the impedance Z may be optionally or additionally obtained from the measurement times for one frequency or a range of frequencies.

Some embodiments of the present disclosure may comprise measuring the impedance using more than one sensor. For example, a set of sensors with the same type of sensing element and different interdigitated array geometry of electrodes may be tested for a same range of frequencies, thereby obtaining different readings of impedance Z and resistance R and capacitance C. The response for different areas may differ, for instance increase, at low and high frequencies. Alternatively or additionally, a set of sensors with different sensing elements may be tested in a range of frequencies, allowing greater selectivity.

A first step of calibration, using known references, may be included in the method. Such calibration step may be important in concentration measurements, for instance, or for embodiments comprising a plurality of interdigitated sensor arrays. Calibration may further comprise measurement of changes in impedance of the sensing element in isolation (e.g. not in contact with gas) for different temperatures. The temperature dependency of the impedance Z, or the resistance R and capacitance C, of the sensing element can be measured while the sensor is closed off from gases, e.g. in vacuum, for a single frequency or a range of frequencies. Changes in impedance Z (or resistance R, capacitance C) stemming from temperature changes (e.g. stemming from the sensor heating up) can be subtracted from the measurement signal, obtaining a temperature-compensated measurement of gas quantity with good selectivity.

Calibration data of resistance R, capacitance C and/or impedance Z may be stored, for example in look-up tables.

In the following, compounds and preparation methods of IL gels for sensing elements are disclosed as exemplary embodiments for the present disclosure. Many different ionic liquids or even mixtures of ionic liquids may be used for production of sensing elements. For example, various ionic liquids and/or mixtures may be used so as to utilize their different affinity towards various gasses. For example, non-water miscible (hydrophobic) ILs may be used in sensors in which it is desirable that only a limited amount of water may be dissolved in the IL (in contrast with fully hydrophilic ionic liquids which absorb water for longer and in higher quantities, which may cause a complete change of phase). The present disclosure is not limited thereto, and hydrophilic ILs may be used in a sensor, e.g. for maintaining high sensitivity in environments with very high humidity, acidity or basicity. Alternatively, sets of ILs with hydrophobic characteristics may be used, which are capable of absorbing small but different amounts of humidity.

Sensing elements according to embodiments of the present disclosure may comprise any of the following ionic liquids, or any mixture thereof, such as: 1-Butyl-3-methyl-imidazolium bis(trifluoromethylsulfonyl)imide, shortened as ([bmim] [NTf2]), 1-Hexyl-3-methyl-imidazolium tris (pentafluoroethyl) trifluorophosphate, shortened as ([hmim][FAP]), 1-butyl-1-methylpyrrolidinium tris(pentafluoroethyl) trifluorophosphate, shortened as ([bmpyl][FAP]), but also compounds comprising trifluoromethanesulfonate or dicyanamide, 1-methyl-3-methylimidazolium dimethylphosphate, 1-butyl-3-methylimidazolium hexafluorophosphate, shortened as ([bmim][$PF_6$]), choline formate, 1-butyl-3-methyl-imidazolium dicyanamide, tri-n-octylmethylammonium chloride, 1-ethyl-3-methyl-imidazolium tetrafluoroborate, shortened as ([emim][$BF_4$]), 1-ethyl-3-methylimidazolium trifluoromethanesulfonate, shortened as ([emim](triflate)), 1-butyl-3-methylimidazolium tetrafluorophosphate, shortened as ([bmim][$PF_4$]), and any mixture thereof. For example, hydrophilic ([emim][$BF_4$]) and ([emim](triflate)) may be mixed with hydrophobic ([bmim][$PF_6$]).

Sensing elements (and IL gels in general) can be categorized, depending on the nature of the underlying gel network, into organic, inorganic or hybrid gels.

Sensing element according to some embodiments of the present disclosure may be formed on top of a substrate comprising electrodes, being held by capillary forces to the substrate. Additionally or alternatively, sensing elements may be obtained in the form of an IL gel by mixing any of the ionic liquids presented, or mixtures thereof, with a gellant. Depending of the nature of the gel network, IL gels may be classified into organic, inorganic or hybrid gels. The following gellants or mixtures thereof may be used in a IL gel: Inorganic gellants, which may include those comprising e.g. Si, Ti or Sn, for example silica-based gels made by inclusions of silica nanoparticles as well as titania and tin oxide-based gels; organic gels, which may be based on small organic gellants and aspartame-based systems, or on biological molecules like sugars or cyclodextrins, as well as polymers and biopolymers, like gelatin, and polysaccharides like cellulose and starch. The choice of IL often determines the type of gellant that is most suitable. For example, poly(methyl methacrylate) (PMMA) is well known to have a high solubility in imidazolium-based ionic liquids (e.g. ([bmim] [NTf2]), or ([hmim][FAP])). Other widely used polymers include poly(ethylene oxide) and fluoropolymers like Nafion and poly(vinylidene fluoride) and poly(vinylidene-co-hexafluoropropylene), or PVdF-HFP in shortened notation, and also polyoxyethylene (20) sorbitan monooleate, dodecanoic acid [2-[(2R,3R,4S)-3,4-dihydroxy-2-tetrahydrofuranyl]-2-hydroxyethyl] ester, poly(styrene-block-ethylene oxideblock-styrene) (SOS) triblock copolymer, 2-hydroxyethyl-methacrylate, poly(propylene oxide)-poly(ethylene oxide)-poly(propylene oxide) (PPO-PEO-PPO) block copolymers (BCPs) with cross-linkable end groups, and any mixture thereof.

The list of gellants and of IL liquids is not exhaustive, and other suitable materials may be used. In the following, few examples of IL gel are given, the present disclosure not being limited to such examples.

The preparation of an exemplary compound suitable for a sensing element in accordance with embodiments of the present disclosure is provided, the present disclosure not being limited by the particular choice of ILs, gellants or solvents, and other methods than the one presented may be also used. Polymer-ion gels may be obtained by dissolving the desired amounts of a suitable IL (such as ([bmim] [NTf2]), ([hmim][FAP]) and ([bmpyl][FAP])) and PVdF-HFP (poly(vinylidene-cohexafluoropropylene (Mw ~400,000 (bimodal distribution), average Mn ~130,000) in acetone or any other suitable solvent. The typical ratio of ionic liquid to PVdf-HFP used here was 80:20 (w/w) but other ratios and gels using other polymers (e.g. PMMA) or even other gelling methods may be used as well. IL gel films were prepared by slow evaporation of a known volume of acetone solution.

Figure 1:
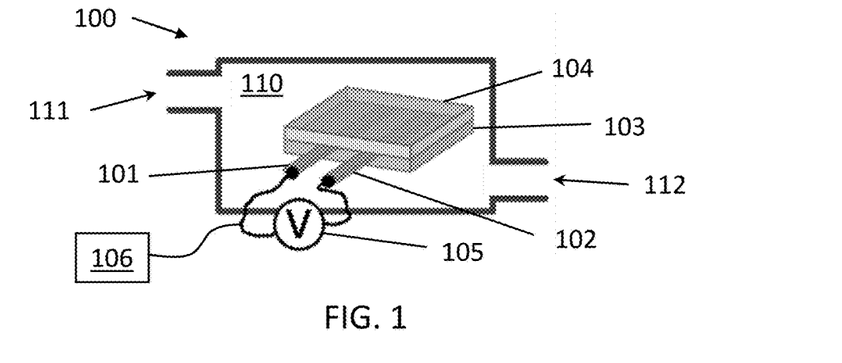
FIG. 1 illustrates a gas sensor with two electrodes, a substrate and a sensing element, according to an example embodiment.

The present exemplary embodiment of IL gel may be applied to a sensor according to embodiments of the present disclosure, such as for instance the exemplary sensor 100 of FIG. 1, the present disclosure not being limited thereto.

In FIG. 1, a pair of conductive electrodes 101, 102, e.g. Pt-electrodes, lay on an insulation carrier 103, e.g. a dielectric substrate, onto which a thin layer of polymer-ionic liquid gel is deposited, forming the sensing element 104. In the example illustrated, as an example only, the electrodes 101, 102 have a width of, e.g. 200 microns, and are separated by a gap of e.g. 400 microns. Other electrode geometries, like for instance interdigitated electrodes, may be applicable as well. The gel in the example presented consists of ([bmim] [NTf2]) and PVdF-co-HFP in a 7:3 weight ratio and is deposited by drop casting from a 52 mg/mL solution in acetone. The electrodes 101, 102 are connected to opposite poles of a power source 105, which in embodiments of the present disclosure may be a variable voltage source, e.g. a voltage source with variable frequency. The present disclosure is not limited thereto, and other power sources and configurations may be employed. For example, one electrode may be connected to the source, while the other may be earthed. Some embodiments of the sensor 100 may further comprise a readout system 106, for analyzing the impedance response, in frequency and/or time, and/or for obtaining the capacitive and resistive components of the impedance. Embodiments of the present disclosure may further comprise e.g. a case 110 with inlet 111 and outlet 112 for gasses.

Figure 2:
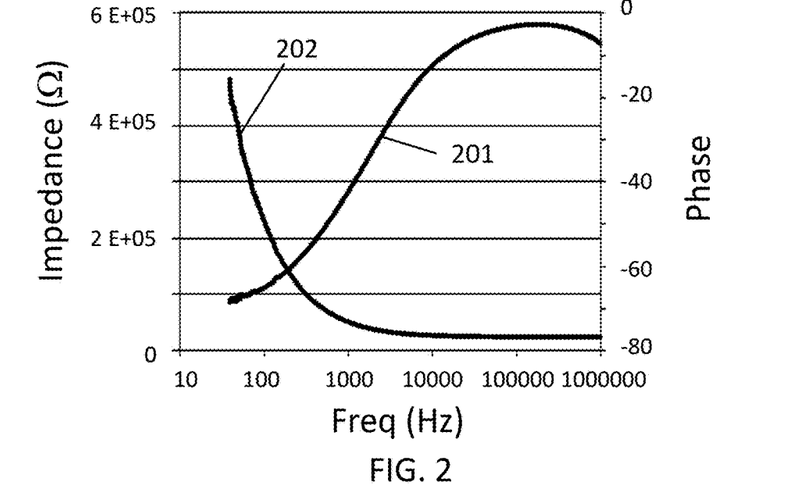
FIG. 2 illustrates the dependence of impedance and phase on measurement frequency, according to an example embodiment.
Figure 3:
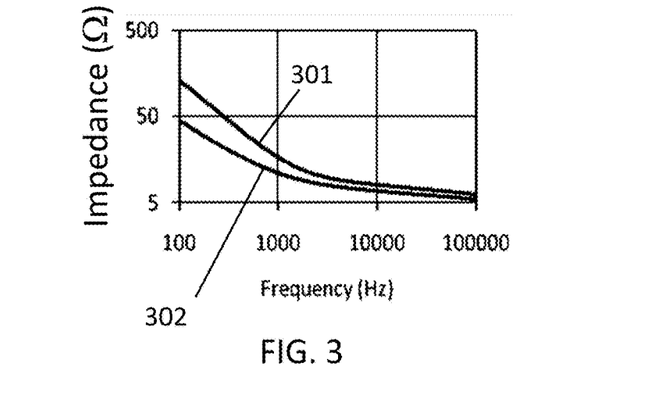
FIG. 3 illustrates the change of impedance with the frequency for a gas in different conditions, according to an example embodiment.

According to embodiments of the second aspect of the present disclosure, the impedance of this IL gel film is measured at various frequencies, for example ranging from 100 Hz to 200 kHz. The results are shown in the graph of FIG. 2 for the phase 201 and the impedance 202. From this figure it can be seen that the impedimetric properties of this gel are a combination of resistive and capacitive behavior. At low frequencies, the response is mainly capacitive, and at high frequencies, the response is mainly resistive. When exposing the sensing element to step-wise changes in gas concentration, a drop in resistive component is observed upon increasing analyte concentration. A typical measurement curve is shown in the graph of FIG. 3, the upper curve 301 being the impedance of the film in dry nitrogen, the lower curve 302 the impedance in humidified nitrogen.

Figure 4:
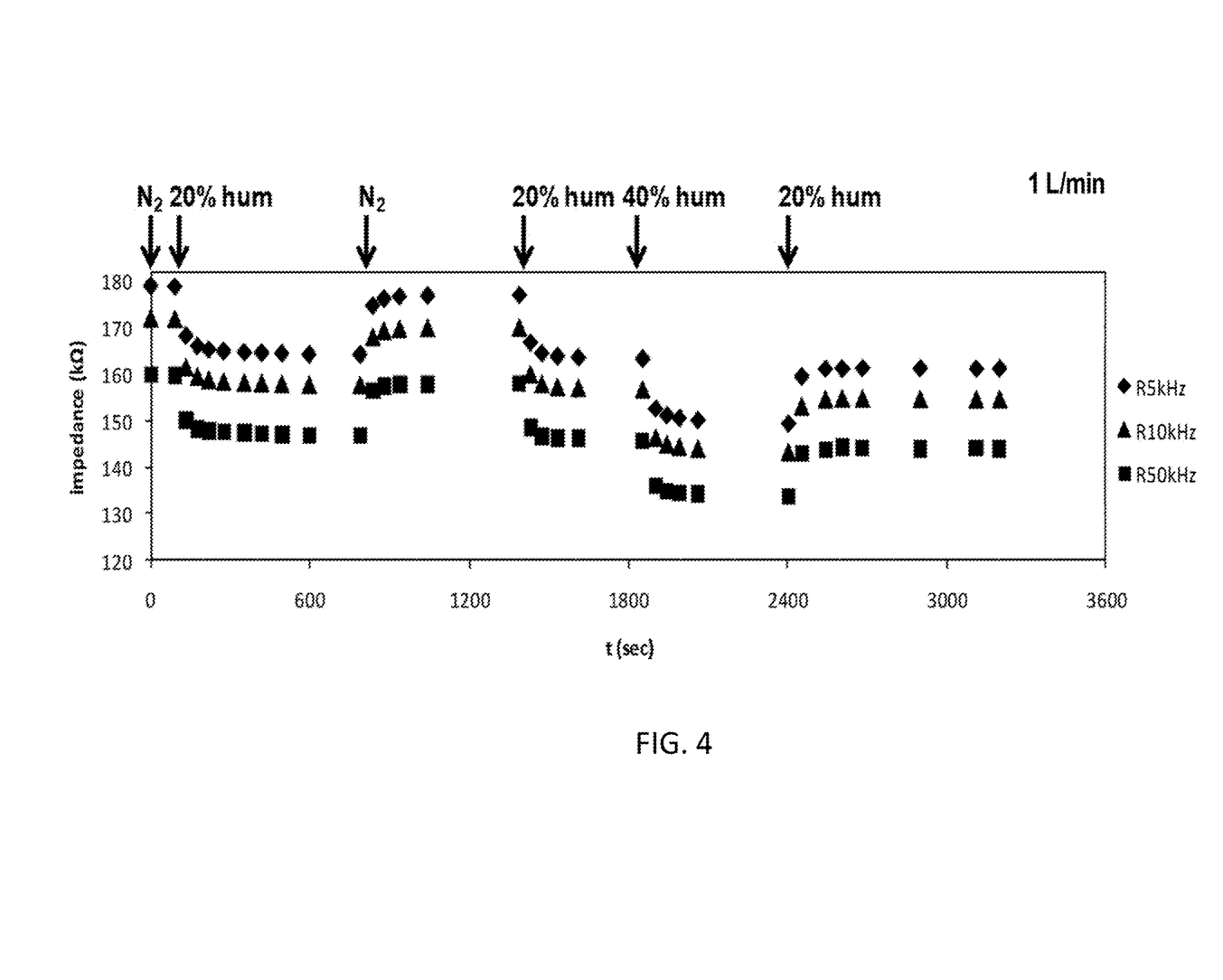
FIG. 4 illustrates the change of impedance with time in a gas being subject to changes in humidity levels, for different frequency levels, according to an example embodiment.

FIG. 4 shows typical impedance-time traces obtained for a film containing ([bmim][NTf2]) and PVdF-co-HFP at 7:3 that is exposed to step-wise changes in humidity levels, for frequencies of 5 kHz, of 10 kHz, and of 50 kHz, at a gas flowrate of 1 L/min. Concentrations and switching times are indicated by arrows above the graph. The sorption is reversible and scales with concentration. The response to humidity (relative humidity, RH) is $3.8 \cdot 10^{-3}$/% RH. This is higher than the response to $CO_2$. but little interference was found because the response to $CO_2$ at 20% RH and 40% RH is $5.8 \cdot 10^{-4}$/% $CO_2$ and $6.7 \; 10^{-4}$/% $CO_2$.

Figure 5:
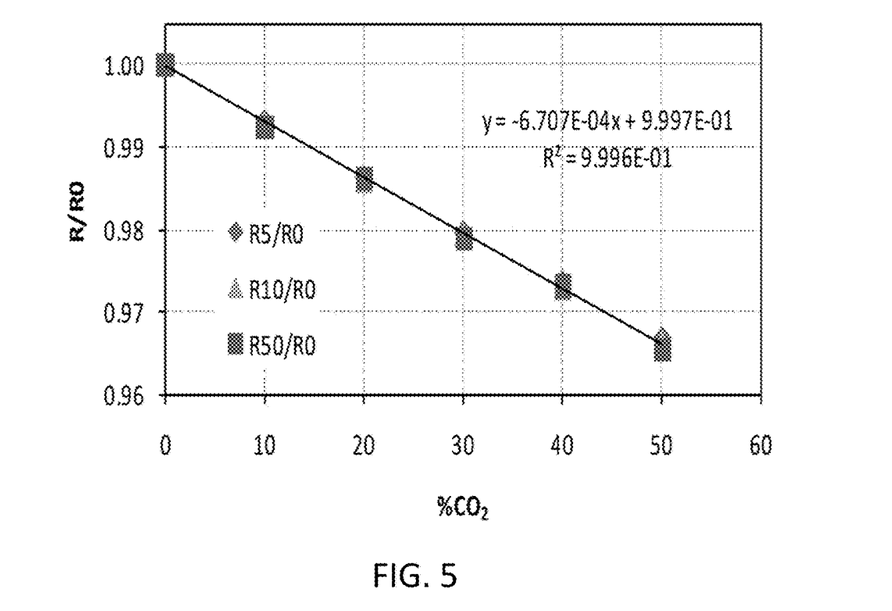
FIG. 5 shows the impedance response, relative to the resistive component, of $CO_2$ concentration, for different frequencies, according to an example embodiment.

FIG. 5 shows that the impedance response, expressed as $R/R_0$ (with $R_0$ being the resistive component in dry nitrogen), is identical for each of the measurement frequencies of FIG. 4 (higher than 5 kHz). From the time-impedance graphs, the sensitivity for humidity, ethanol, $CO_2$, and $O_2$ has been determined at:

Humidity (in air): $\Delta R/R = 3.8 \cdot 10^{-3}$/% RH~$1.6 \cdot 10^{-5}$/ppm (20° C.)

Ethanol (in dry air): $\Delta R/R = 1 \cdot 10^{-6}$/ppm $CO_2$ (in dry air): $\Delta R/R = 0.067 \cdot 10^{-6}$/ppm $CO_2$ (in air with 20% RH): $\Delta R/R = 0.058 \cdot 10^{-6}$/ppm $CO_2$ (in air with 20% RH): $\Delta R/R = 0.067 \cdot 10^{-6}$/ppm $O_2$: No response By changing the electrode design from two simple parallel electrodes to an interdigitated electrode design, the sensitivity towards $CO_2$ may be improved to $0.2 \cdot 10^{-6}$/ppm.

As shown above, the impedance can be used as a method to measure the concentration of a number of gasses and vapors. At high frequencies (i.e. in the regime where the resistive properties of the sensing element govern the response) the measured impedance scales with the concentration of analyte (e.g. gas in the IL gel). At lower frequencies (i.e where the capacitive properties of the film are dominant in the response) the sensitivity is very different. For example for humidity the response at high frequencies has a sensitivity of $0.4 \; 10^{-3}$ per % RH. At low frequencies the sensitivity is approximately 5-fold higher. By operating the sensor at lower frequency a higher sensitivity can be obtained.

200 Hz $\Delta R/R = 0.14 \cdot 10^{-3}$/% RH

Figure 6:
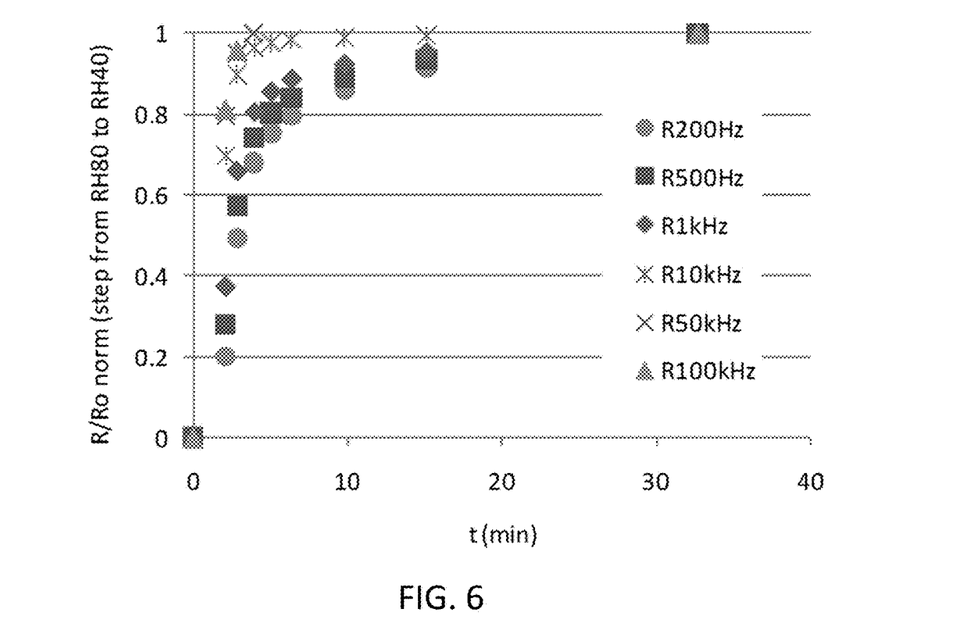
FIG. 6 illustrates the response time of a sensor to a humidity change for a range of frequencies, according to an example embodiment.

500 Hz $\Delta R/R = 0.11 \cdot 10^{-3}$/% RH 1 kHz ΔR/R=0.076·10⁻³/% RH
10 kHz ΔR/R=0.042·10⁻³/% RH
50 kHz ΔR/R=0.042·10⁻³/% RH
100 kHz ΔR/R=0.031·10⁻³/% RH FIG. 6 shows the response of the sensor to a step-wise change in humidity from 80 to 40% RH (switch time is at t=2 min). The time for the high frequency signal (the resistive component of the response) to saturate is very short (<3 min) whereas at low frequencies the signal is saturated only after more than 20 minutes.

Hence, it is shown that different responses (resistance R and capacitance C) at various frequencies may be used to obtain selectivity within a single sensor. Alternatively, a set of sensors with different electrode designs or different sensing elements may be employed, in which each of the sensors are tailored towards optimizing the response for either the resistive or the capacitive component.

Figure 7:
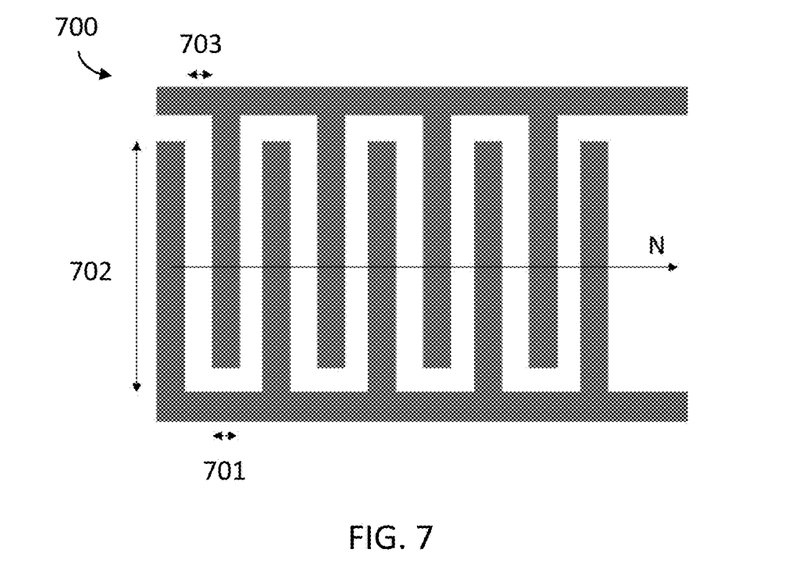
FIG. 7 illustrates an embodiment of interdigitated array of electrodes, according to an example embodiment.

An example of interdigitated electrode 700 design which may be used in embodiments of the present disclosure, is shown in FIG. 7. A number of variations is possible in the design of the electrodes: the number N of interdigitating electrode fingers may be varied (2≤N< . . . ), the width 701 and length 702 of each finger, and the separation 703 of each of the fingers of the electrodes can be tailored in order to optimize the resistive and/or capacitive components of the sensor response. Such design variations may be obtained by modelling and optimization, for example, and calibration. In some embodiments of the present disclosure, the interdigitated array comprises microelectrodes (IDAM). The microelectrodes can be formed by any suitable technique such as patterning, etching, laser trimming, microwelding, selective deposition, etc.

Figure 8:
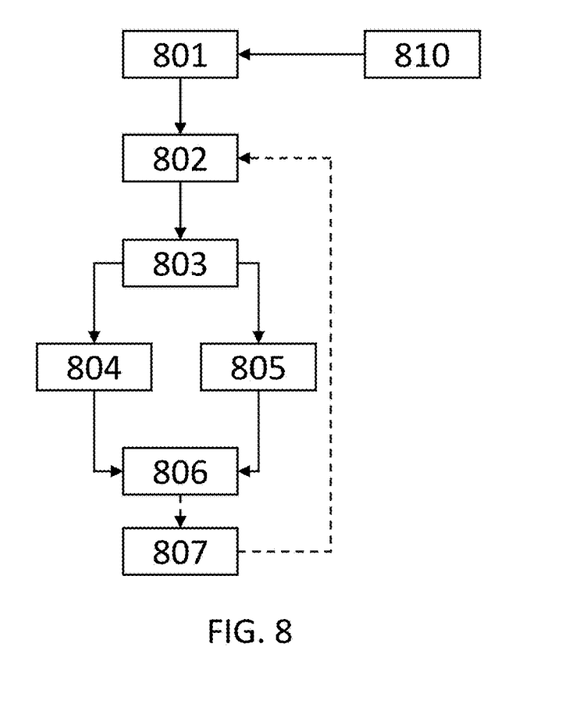
FIG. 8 illustrates a block diagram of a method for measuring the concentration of gasses, according to an example embodiment.

FIG. 8 shows in a flowchart an example of a method according to some embodiments of the second aspect of the present disclosure, for measuring the concentration of one or more gasses using a sensor or sensor system according to the first aspect of the present disclosure. A pre-calibration step 810 may be performed, e.g. measurement of impedance changes with temperature and in isolation of gasses, for temperature compensation, or measurement of known analytes at known concentrations. Then, the sensor is exposed 801 to a gas or environment. The sensing element is polarized 802 with a variable electrical signal at a predetermined frequency; and the impedance response is measured 803, for example for a period of time. For example, the resistive component may be obtained 804 after or for a period of time, and the capacitive component may also be obtained 805 after a period of time, or the capacitive component may be recorded for a period of time. By comparison with look-up tables or calibration data, the composition and even the concentration of the gas may be obtained 806. The measurement can be repeated 807 for different frequencies.

The invention claimed is:

1. A gas sensor comprising:
   at least one sensing element comprising an ionic liquid;
   at least one pair of electrodes coupled to the at least one sensing element;
   an electric power source configured to provide a frequency-controllable electrical AC signal to the at least one pair of electrodes so as to generate an impedimetric response signal from the at least one sensing element; and
   readout circuitry configured to analyze resistive and capacitive components of the impedimetric response signal.

2. The gas sensor according to claim 1, wherein the at least one sensing element comprises an ionic liquid gel formed of a gellant and the ionic liquid.

3. The gas sensor according to claim 2, wherein the gellant is selected from the group consisting of: organic gels, inorganic gels, or a mixture thereof.

4. The gas sensor according to claim 1, wherein the at least one pair of electrodes form an interdigitated array of electrodes.

5. The gas sensor according to claim 1, wherein the at least one sensing element further comprises a plurality of ionic liquids.

6. The gas sensor according to claim 1, wherein the ionic liquid is selected from the group consisting of: 1-Butyl-3-methylimidazolium bis(trifluoromethylsulfonyl)imide, 1-Hexyl-3-methylimidazolium tris(pentafluoroethyl) trifluorophosphate, and 1-butyl-1-methylpyrrolidinium tris(pentafluoroethyl)trifluorophosphate.

7. The gas sensor according to claim 6, wherein the at least one sensing element comprises 1-Butyl-3-methylimidazolium bis(trifluoromethylsulfonyl)imide and poly(vinylidene-co-hexafluoropropylene) in a 7:3 weight ratio.

8. The gas sensor according to claim 1, wherein the electric power source is adapted for providing an electric AC signal with a frequency of at least 0.1 Hz.

9. The gas sensor according to claim 1, comprising at least a first and a second sensing element, wherein the first sensing element comprises a first pair of electrodes comprising an interdigitated electrode array with a predetermined first geometry, and wherein the second sensing element comprises a second pair of electrodes comprising an interdigitated electrode array with a predetermined second geometry different from the first geometry.

10. The gas sensor according to claim 9, further comprising an interdigitated array of electrodes for each sensing element, wherein a number of electrodes and dimensions thereof in the array are adapted to optimize either a resistive component or a capacitive component of an impedance of each sensing element.

11. The gas sensor according to claim 9, wherein each sensing element comprises a same ionic liquid gel, and the electric power source is shared by each sensing elements.

12. The gas sensor according to claim 1, wherein the capacitive component of the impedimetric response signal is based on an interface between the at least one pair of electrodes and the sensing element, and wherein the resistive component of the impedimetric response signal is based on bulk properties of the sensing element.

13. A method comprising:
   exposing at least one gas sensor to a gas or gas mixture, wherein the at least one gas sensor comprises at least one sensing element comprising an ionic liquid;
   providing an electrical AC signal at a first frequency to the at least one sensing element by way of at least one pair of electrodes, wherein the at least one sensing element generates an impedimetric response signal;
   measuring the impedimetric response signal of the at least one sensing element;
   separating the impedimetric response signal into resistive and capacitive components;
   determining a composition of the gas or gas mixture based at least on the resistive and capacitive components; and
   repeating measuring the impedimetric response signal for at least a further frequency different from the first frequency, wherein the further frequency is between 100 Hz and 200 kHz.

14. The method according to claim 13, further comprising comparing the resistive and capacitive components to a look-up table and wherein determining the composition of the gas or gas mixture is further based on the comparison.

15. The method according to claim 13, further comprising calibrating with a known reference to obtain calibration data.

16. The method according to claim 15, further comprising comparing the resistive and capacitive components to the calibration data and wherein determining the composition of the gas or gas mixture is further based on the comparison.

17. The method according to claim 13, wherein the at least one gas sensor comprises at least a first and a second sensing element, wherein the first sensing element comprises a first pair of electrodes comprising an interdigitated electrode array with a predetermined first geometry, and wherein the second sensing element comprises a second pair of electrodes comprising an interdigitated electrode array with a predetermined second geometry different from the first geometry.

18. The method according to claim 17, wherein the at least one gas sensor further comprises an interdigitated array of electrodes for each sensing element, wherein a number of electrodes and dimensions thereof in the array are adapted to optimize either a resistive component or a capacitive component of an impedance of each sensing element.

* * * * *